United States Patent [19]

Perronnet et al.

[11] 4,067,720
[45] Jan. 10, 1978

[54] CERTAIN 2-CARBAMOYL-1,2,4-THIADIAZOLE-3-ONE HERBICIDES

[75] Inventors: Jacques Perronnet, Paris; Laurent Taliani, Les Pavillons-sous-Bois; André Tèche, Nanterre, all of France

[73] Assignee: Roussel Uclaf, Paris, France

[21] Appl. No.: 679,334

[22] Filed: Apr. 22, 1976

[30] Foreign Application Priority Data

Apr. 24, 1975 France .............................. 75.12787

[51] Int. Cl.² ...................... C07D 285/08; A01N 9/12
[52] U.S. Cl. ................................. 71/90; 260/302 SD; 260/302 D; 260/306.8 D; 260/465 E; 260/465.5 R
[58] Field of Search ..... 260/302 D, 302 SD, 306.8 D; 71/90

[56] References Cited

U.S. PATENT DOCUMENTS 3,574,226  4/1971  Ratz et al. ..................... 260/302 D
3,994,909  11/1976  Pommer et al. ................. 260/302 D Primary Examiner—Richard J. Gallagher
Attorney, Agent, or Firm—Hammond & Littell

[57] ABSTRACT

Novel thiadiazoles of the formula

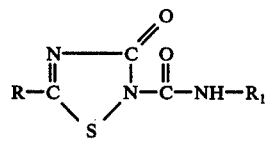

I wherein R is selected from the group consisting of alkoxy of 1 to 8 carbon atoms, cycloalkyloxy of 3 to 7 carbon atoms, alkylthio of 1 to 8 carbon atoms optionally substituted with carbalkoxy of 2 to 5 carbon atoms, alkenylthio of 2 to 4 carbon atoms,

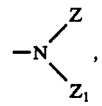

and benzyloxy, benzylthio, benzyl and phenyl, all aryl being optionally substituted with 1 to 2 members of the group consisting of chlorine, bromine, alkyl of 1 to 3 carbon atoms and alkoxy of 1 to 3 carbon atoms, Z and $Z_1$ are alkyl of 1 to 4 carbon atoms and $R_1$ is selected from the group consisting of alkyl of 1 to 6 carbon atoms optionally substituted with a member of the group consisting of chlorine, bromine and alkyloxy of 1 to 4 carbon atoms, phenyl optionally substituted with 1 to 2 members of the group consisting of bromine, chlorine, alkyl of 1 to 3 carbon atoms and alkoxy of 1 to 3 carbon atoms, alkenyl of 2 to 4 carbon atoms optionally substituted with at least one member of the group consisting of chlorine and alkoxy of 1 to 3 carbon atoms,

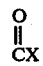

and carbalkoxy of 2 to 6 carbon atoms and X is selected from the group consisting of alkyl of 1 to 4 carbon atoms and alkenyl of 2 to 4 carbon atoms, both optionally substituted with at least one chlorine having herbicidal properties and novel intermediates.

18 Claims, No Drawings

CERTAIN 2-CARBAMOYL-1,2,4-THIADIAZOLE-3-ONE HERBICIDES

STATE OF THE ART

Copending, commonly assigned U.S. patent application Ser. No. 517,379 filed Oct. 23, 1974 (now abandoned) describes 3-phosphoryloxy-1,2,4-thiadiazoles as insecticides as well as U.S. Pat. Nos. 3,574,223 and 3,801,586.

OBJECTS OF THE INVENTION

It is an object of the invention to provide the novel 1,2,4-thiadiazole-3-ones of formula I.

It is another object of the invention to provide a novel process for the preparation of the compounds of formula I and to novel intermediates therefor.

It is a further object of the invention to provide novel herbicidal compositions and to provide a novel method of killing plants.

These and other objects and advantages of the invention will become obvious from the following detailed description.

THE INVENTION

The novel 1,2,4-thiadiazole-3-ones of the invention have the formula

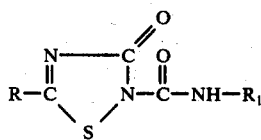

wherein R is selected from the group consisting of alkoxy of 1 to 8 carbon atoms, cycloalkyloxy of 3 to 7 carbon atoms, alkylthio of 1 to 8 carbon atoms optionally substituted with carbalkoxy of 2 to 5 carbon atoms, alkenylthio of 2 to 4 carbon atoms,

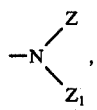

and benzyloxy, benzylthio, benzyl and phenyl, all aryl being optionally substituted with 1 to 2 members of the group consisting of chlorine, bromine, alkyl of 1 to 3 carbon atoms and alkoxy of 1 to 3 carbon atoms, Z and $Z_1$ are alkyl of 1 to 4 carbon atoms and $R_1$ is selected from the group consisting of alkyl of 1 to 6 carbon atoms optionally substituted with a member of the group consisting of chlorine, bromine and alkyloxy of 1 to 4 carbon atoms, phenyl optionally substituted with 1 to 2 members of the group consisting of bromine, chlorine, alkyl of 1 to 3 carbon atoms and alkoxy of 1 to 3 carbon atoms, alkenyl of 2 to 4 carbon atoms optionally substituted with at least one member of the group consisting of chlorine and alkoxy of 1 to 3 carbon atoms,

and carbalkoxy of 2 to 6 carbon atoms and X is selected from the group consisting of alkyl of 1 to 4 carbon atoms and alkenyl of 2 to 4 carbon atoms, both optionally substituted with at least one chlorine.

Examples of suitable substituents for R in formula I are methoxy, ethoxy and branched or straight chain propoxy, butoxy, pentyloxy, hexyloxy, heptyloxy or octyloxy; cyclopropyloxy, cyclopentyloxy, cyclohexyloxy or cycloheptyloxy; methylthio, ethylthio and branched or straight chain propylthio, butylthio, pentylthio and hexylthio; methoxycarbonylmethylthio, ethoxycarbonylmethylthio, propoxycarbonylmethylthio, methoxycarbonylethylthio, ethoxycarbonylethylthio and propoxycarbonylethylthio; allylthio; benzyloxy, benzylthio, phenyl and benzyl optionally substituted in the 3 or 4-position with chlorine or bromine, 2 bromine or chlorine in the 3 and 4 positions, methyl in the 3- and/or 4-position and methoxy in the 3- and/or 4-position; or dimethylamino, diethylamino, dipropylamino or dibutylamino.

Examples of $R_1$ for the compounds of formula I are methyl, ethyl and branched or straight chain propyl, butyl, pentyl or hexyl; methoxyethyl, ethoxyethyl, propoxyethyl or butoxyethyl; phenyl, 3-chlorophenyl, 4-chlorophenyl, 3,4-dichlorophenyl, 3-bromophenyl, 4-bromophenyl, 3,4-dibromophenyl, 3-methylphenyl, 4-methylphenyl, 3,4-dimethylphenyl, 3-methoxyphenyl, 4-methoxyphenyl or 3,4-dimethoxyphenyl; vinyl, allyl, 1-chlorovinyl, 2-chlorovinyl, 1,2-dichlorovinyl and 1,2,2-trichlorovinyl; and 3-oxo-buten-1-yl and 3-oxo-penten-1-yl.

Among the preferred compounds of formula I, $R_1$ is alkyl of 1 to 6 carbon atoms optionally substituted with chlorine, bromine or alkyloxy of 1 to 4 carbon atoms and $R_1$ is most preferably alkyl of 1 to 6 carbon atoms when R is alkyloxy of 1 to 8 carbon atoms, alkylthio of 1 to 8 carbon atoms or alkenylthio of 2 to 4 carbon atoms.

The novel process of the invention for the preparation of the 1,2,4-thiadiazole-3-ones of formula I comprises reacting a compound of the formula

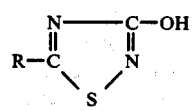

wherein R has the above definition with an isocyanate of the formula $$R_1-N=C=O \qquad \text{III}$$

wherein $R_1$ has the above definition. The condensation reaction is preferably effected in the presence of a tertiary base such as triethylamine or pyridine in an organic solvent such as ethyl ether, isopropyl ether, tetrahydrofuran, benzene or chloroform.

The starting materials of formula II may be prepared by reacting a compound of the formula

wherein R has the above definition and X is an alkali metal such as sodium or potassium with an oxidizing agent, preferably hydrogen peroxide or by reacting a compound of the formula

wherein R and X have the above definition with chloramine.

Some of the compounds of formula II are described in Belgium Pat. No. 821,420 but 3-hydroxy-5-benzyl-1,2,4-thiadiazole, 3-hydroxy-5-ethoxy carbonylmethylthio-1,2,4-thiadiazole, 3-hydroxy-5-n-butylthio-1,2,4-thiadiazole, 3-hydroxy-5-cyclohexyloxy-1,2,4-thiadiazole, 3-hydroxy-5-n-hexyloxy-1,2,4-thiadiazole and 3-hydroxy-5-isopropoxy-1,2,4-thiadiazole are novel. Other novel intermediates are sodium O-cyclohexyl-N-cyanothioimido-carbonate, O-n-hexyl-S-methyldithio-carbonate, potassium O-n-hexyl-N-cyanothioimidocarbonate, and potassium O-isopropyl-N-cyanothioimidocarbonate.

The novel herbicidal compositions of the invention are comprised of an herbicidally effective amount of at least one compound of formula I and an inert carrier. The compositions usually contain 10 to 80% by weight of the compounds of formula I and may also contain one or more other pesticidal agents or compounds which influence the growth of plants.

The compositions may be in the form of powders, granules, suspensions, emulsions or solutions containing the active ingredient and other components such as cationic, anionic or non-ionic surface active agents, inert powders such as talc, clays, silicates or kieselguhr and a vehicle such as water, alcohol, hydrocarbons or other organic solvents or a vegetable, animal or mineral oil.

The method of the invention of killing plants comprises contacting the plants with an herbicidally effective amount of at least one compound of formula I. The said compound can be applied post or pre-emergence and the usual useful dose is 10 to 0.3 kg/ha depending on the product, the plant to be treated and the method of application.

In the following examples there are described several preferred embodiments to illustrate the invention. However, it is to be understood that the invention is not intended to be limited to the specific embodiments.

EXAMPLE 1

2-(methylcarbamoyl)-5-benzyl-1,2,4-thiadiazole-3-one

STEP A: 3-hydroxy-5-benzyl-1,2,4-thiadiazole 0.5 g of phenolphthalein were added to a solution of 70 g of potassium N-cyanoiminobenzyl thioformate [described by Hartle et al., Arch. Pharm., Vol. 308 (1970), p. 625] in 200 ml of water and 66 ml of hydrogen peroxide (110 volumes) were added thereto over 2 hours with stirring while keeping the pH basic by adding 3 times over the course of the addition 3 ml of potassium hydroxide. The mixture was stirred for 30 minutes at 20° C and was then acidified to a pH of 4 by addition of acetic acid. The mixture stood for an hour at 20° C and was then vacuum filtered. The recovered crystals were washed with ether and dried to obtain 5 g of 3-hydroxy-5-benzyl-1,2,4-thiadiazole melting at 58° C. The mother liquors were extracted with chloroform and the extracts were treated with activated carbon, filtered, dried and concentrated to dryness under reduced pressure to obtain 26 g of 3-hydroxy-5-benzyl-1,2,4-thiadiazole melting at 50° C. The said product was used as is for the next step.

STEP B: 2-(methylcarbamoyl)-5-benzyl-1,2,4-thiadiazole-3-one 50 ml of methyl isocyanate were added to a solution of 15 g of 3-hydroxy-5-benzyl-1,2,4-thiadiazole in 400 ml of isopropyl ether and the mixture was stirred at 20° C for 72 hours. 50 ml of chloroform were added thereto and the mixture was vacuum filtered. The recovered crystals were dried to obtain 10 g of 2-(methylcarbamoyl)-5-benzyl-1,2,4-thiadiazole-3-one melting at 146° C.

Analysis: $C_{11}H_{11}N_3O_2S$: Calculated: %C 52.99, %H 4.44, %N 16.85, %S 12.86; Found: C 52.9, H 4.5, N 17.0, S 12.9.

EXAMPLE 2

2-(N-ethylcarbamoyl)-5-n-butoxy-1,2,4-thiadiazole-3-one

STEP A: sodium O-n-butyl-N-cyanothioimidocarbonate 380 g of carbon disulfide were added at 20°–30° C to a mixture of 280 g of potassium hydroxide pellets in 2.5 liters of butanol and the mixture was stirred for 2 hours and was then vacuum filtered. The precipitate was washed with butanol and then ether to obtain 640 g of potassium O-n-butyldithiocarbonate melting at 260° C (dec.). A mixture of 190 g of said product, 1000 ml of benzene and 500 ml of methyl iodide was refluxed for 10 hours and was then filtered. The filtrate was evaporated to dryness and the residue was rectified to obtain 156 g of methyl O-n-butyl-dithiocarbonate with a boiling point of 74° C at 0.5 mm Hg.

42 g of cyanamide were added at 20° C to a solution of 55 g of sodium methylate in 360 ml of methanol and 360 ml of ethanol and then 164 g of methyl O-n-butyl-dithiocarbonate were added. The mixture was stirred at 20° C for 17 hours and was evaporated to dryness. The residue was washed with ether to obtain 120 g of sodium O-n-butyl-N-cyanothioimidocarbonate melting at 240° C.

STEP B: 3-hydroxy-5-n-butoxy-1,2,4-thiadiazole 80 ml of 30% hydrogen peroxide were added at 80°–85° C to a mixture of 72 g of sodium O-n-butyl-N-cyanothioimidocarbonate, 200 ml of water and 500 mg of phenolphthalein while maintaining the pH basic by addition of sodium hydroxide and the mixture was cooled and vacuum filtered to obtain the sodium salt of 3-hydroxy-5-n-butoxy-1,2,4-thiadiazole. The said salt was suspended in 100 ml of water and the mixture was made acidic by hydrochloric acid addition. The mixture was extracted with ethyl acetate to obtain 58 g of 3-hydroxy-5-n-butoxy-1,2,4-thiadiazole melting at 62° C.

STEP C: 2-(N-ethylcarbamoyl)-5-n-butoxy-1,2,4-thiadiazole-3-one 1 ml of triethylamine was added to a solution of 17.4 g of 3-hydroxy-5-n-butoxy-1,2,4-thiadiazole in 150 ml of tetrahydrofuran and then 12 ml of ethyl isocyanate were added dropwise with stirring. The mixture was stirred for 2 hours at 20° C and was concentrated to dryness under reduced pressure. The residue was chromatographed over silica gel and elution with a 7-3 benzene-ethyl acetate mixture yielded 18.5 g of 2-(N-ethylcarbamoyl)-5-n-butoxy-1,2,4-thiadiazole-3-one.

Analysis: $C_9H_{15}N_3O_3S$: Calculated: %C 44.06, %H 6.16, %N 17.13, %S 13.07; Found: C 44.1, H 6.2, N 16.9, S 13.3.

EXAMPLE 3

2-(N-n-butylcarbamoyl)-5-ethoxy-1,2,4-thiadiazole-3-one

STEP A: 3-hydroxy-5-ethoxy-1,2,4-thiadiazole 130 ml of 30% hydrogen peroxide were added in 10 ml fractions to a mixture of 200 g of potassium O-ethyl-N-cyanothioimidocarbonate in 800 ml of water and after returning the mixture to room temperature, 30 g of sodium bicarbonate were added. The solution was washed with 500 ml of ethyl acetate and the pH was adjusted to 3 by addition of concentrated hydrochloric acid. The mixture was extracted with ethyl acetate and the extracts were dried over sodium sulfate and evaporated to dryness. The 85 g of oil were crystallized from 200 ml of ether and then from benzene to obtain 28 g of 3-hydroxy-5-ethoxy-1,2,4-thiadiazole melting at 98° C.

STEP B: 2-(N-n-butylcarbamoyl)-5-ethoxy-1,2,4-thiadiazole-3-one 12 ml of triethylamine were added to a solution of 26.4 g of 3-hydroxy-5-ethoxy-1,2,4-thiazole in 110 ml of tetrahydrofuran and 34 g of n-butyl isocyanate were added thereto over 5 minutes at 20° C. The mixture was stirred for an hour at 20° C and was concentrated to dryness under reduced pressure. The residue was added to isopropyl ether and the solution was cooled to −20° C and vacuum filtered. The recovered precipitate was washed, dried and crystallized from ethyl acetate to obtain 22 g of 2-(N-n-butylcarbamoyl)-5-ethoxy-1,2,4-thiadiazole-3-one melting at 54° C.

Analysis: $C_9H_{15}N_3O_3S$: Calculated: %C 44.07, %H 6.17, %N 17.13, %S 13.07; Found: C 44.0, H 6.2, N 17.3, S 12.7.

EXAMPLE 4

2-(N-methylcarbamoyl)-5-ethoxy-1,2,4-thiadiazole-3-one 6 g of triethylamine and 9 ml of methyl isocyanate were added to a solution of 13.2 g of 3-hydroxy-5-ethoxy-1,2,4-thiadiazole-3-one in 60 ml of tetrahydrofuran and the mixture was stirred for an hour at 20° C, cooled to 0° C and vacuum filtered. The recovered crystals were crystallized from ethyl acetate to obtain 14.4 g of 2-(N-methylcarbamoyl)-5-ethoxy-1,2,4-thiadiazole-3-one melting at 152° C.

Analysis: $C_6H_9N_3O_3S$: Calculated: %C 35.46, %H 4.46, %N 20.68, %S 15.78; Found: C 35.7, H 4.4, N 20.7, S 15.9.

EXAMPLE 5

2-(N-m-chlorophenylcarbamoyl)-5-ethoxy-1,2,4-thiadiazole-3-one 43 g of 3-chlorophenyl isocyanate were added to a solution of 29.4 g of 3-hydroxy-5-ethoxy-1,2,4-thiadiazole in 300 ml of tetrahydrofuran and the mixture was stirred for 2½ hours at 20° C. The mixture was evaporated to dryness under reduced pressure and the residue was crystallized from ethyl acetate to obtain 26 g of 2-(N-m-chlorophenylcarbamoyl)-5-ethoxy-1,2,4-thiadiazole-3-one melting at 141° C.

Analysis: $C_{11}H_{10}ClN_3O_3S$: Calculated: %C 44.07, %H 3.36, %N 14.02, %S 10.70, %CL 11.82; Found: C 44.1, H 3.3, N 13.9, S 10.8, Cl 11.8.

EXAMPLE 6

2-(N-β-chloroethylcarbamoyl)-5-ethoxy-1,2,4-thiadiazole-3-one 41 g of β-chloroethyl isocyanate were added to a solution of 28.7 g of 3-hydroxy-5-ethoxy-1,2,4-thiadiazole in 500 ml of benzene and after stirring for 17 hours at 20° C, the mixture was filtered. The filtrate was evaporated to dryness and the residue was empasted with isopropyl ether and was dried to obtain 47 g of 2-(N-β-chloroethylcarbamoyl)-5-ethoxy-1,2,4-thiadiazole-3-one melting at 82° C.

Analysis: $C_7H_{10}N_3ClO_3S$: Calculated: %C 33.40, %H 4.00, %Cl 14.08, %N 16.70, %S 12.74; Found: C 33.3, H 4.0, Cl 14.4, N 16.7, S 12.9.

EXAMPLE 7

2-(N-β-ethoxyethylcarbamoyl)-5-ethoxy-1,2,4-thiadiazole-3-one 1 ml of triethylamine was added to a solution of 14.6 g of 3-hydroxy-5-ethoxy-1,2,4-thiadiazole in 140 ml of tetrahydrofuran and then 23 g of ethoxyethyl isocyanate were added dropwise. The mixture was stirred for 2 hours at 25° C and was concentrated to dryness. The residue was chromatographed over silica gel and elution with a 4–6 benzene-ethyl acetate mixture yielded 14 g of 2-(N-β-ethoxyethylcarbamoyl)-5-ethoxy-1,2,4-thiadiazole-3-one melting at <50° C.

Analysis : $C_9H_{15}N_3O_4S$ : Calculated : %C 41.37, %H 5.78, %N 16.08, %S 12.27; Found : C 41.1, H 6.0, N 16.1, S 12.1.

EXAMPLE 8

2-(N-trichlorovinylcarbamoyl)-5-ethoxy-1,2,4-thiadiazole-3-one 51.7 g of trichlorovinyl isocyanate were added dropwise to a solution of 21.9 g of 3-hydroxy-5-ethoxy-1,2,4-thiadiazole in 300 ml of benzene and after stirring the mixture for 16 hours at 20° C, the mixture was filtered. The filtrate was evaporated to dryness and the product was eluted with 7-3 benzene-ethyl acetate mixture and crystallized from isopropyl ether to obtain 22 g of 2-(N-trichlorovinylcarbamoyl)-5-ethoxy-1,2,4-thiadiazole-3-one melting at 123° C.

Analysis: $C_7H_6Cl_3N_3O_3S$: Calculated: %C 26.39, %H 1.90, %Cl 33.39, %N 13.19, %S 10.00; Found: C 26.6, H 2.0, Cl 33.2, N 13.5, S 10.3.

EXAMPLE 9

2-(N-α-chloroacetylcarbamoyl)-5-ethoxy-1,2,4-thiadiazole-3-one 31.5 g of α-chloroacetyl isocyanate were added dropwise to a solution of 18.98 g of 3-hydroxy-5-ethoxy-1,2,4-thiadiazole in 200 ml of benzene and after stirring the mixture for 17 hours at 20° C, it was vacuum filtered. The recovered crystals were dried to obtain 20 g of 2-(N-α-chloroacetylcarbamoyl)-5-ethoxy-1,2,4-thiadiazole-3-one melting at 132° C.

Analysis: $C_7H_8ClN_3O_4S$: Calculated: %C 31.65, %H 3.03, %Cl 13.34, %N 15.82, %S 12.07; Found: C 31.7, H 3.0, Cl 13.3, N 16.0, S 12.4.

EXAMPLE 10

2-(N-ethoxycarbonylcarbamoyl)-5-ethoxy-1,2,4-thiadiazole-3-one 23 g of ethoxycarbonyl isocyanate were added dropwise to a solution of 14.6 g of 3-hydroxy-5-ethoxy-1,2,4-thiadiazole in 140 ml of tetrahydrofuran containing 1 ml of triethylamine and the mixture was stirred for 1½ hours at 20° C and was filtered. The filtrate was concentrated to dryness and the residue was empasted with isopropyl ether and vacuum filtered. The product was crystallized from ethyl acetate to obtain 18 g of 2-(N-ethoxycarbonylcarbamoyl)-5-ethoxy-1,2,4-thiadiazole-3-one melting at 119° C.

Analysis: $C_8H_{11}N_3O_5S$: Calculated %C 36.78, %H 4.24, %N 16.08, %S 12.27; Found: C 36.7, H 4.3, N 16.2, S 12.5.

EXAMPLE 11

2-(N-m-chlorophenylcarbamoyl)-5-ethylthio-1,2,4-thiadiazole-3-one

STEP A: 3-hydroxy-5-ethylthio-1,2,4-thiadiazole

Dipotassium N-cyano-dithioimidocarbonate and diethyl sulfate were condensed in an aqueous media and the product was reacted with hydrogen peroxide to obtain 3-hydroxy-5-ethylthio-1,2,4-thiadiazole melting at 129° C.

STEP B: 2-(N-m-chlorophenylcarbamoyl)-5-ethylthio-1,2,4-thiadiazole-3-one 23 g of m-chlorobenzoyl isocyanate were added over 15 minutes to a solution of 24.3 g of 3-hydroxy-5-ethylthio-1,2,4-thiadiazole in 250 ml of tetrahydrofuran and the mixture was stirred for 17 hours at 20° C and was filtered. The pasty product was washed with tetrahydrofuran and dried to obtain 41 g of 2-(N-m-chlorophenylcarbamoyl)-5-ethylthio-1,2,4-thiadiazole-3-one melting at 168° C. The product was crystallized from methyl ethyl ketone for a microanalytically pure sample melting at 168° C.

Analysis: $C_{11}H_{10}ClN_3O_2S_2$: Calculated: %C 41.83, %H 3.19, %Cl 11.23, %N 13.30, %S 20.31; Found: C 42.1, H 3.1, Cl 11.1, N 13.5, S 20.2.

EXAMPLE 12

2-(N-methylcarbamoyl)-5-(ethoxycarbonylmethylthio)-1,2,4-thiadiazole-3-one

STEP A: 3-hydroxy-5-(ethoxycarbonylmethylthio)-1,2,4-thiadiazole 500 ml of methanol were added to a solution of 118 g of potassium N-cyanoimidodithiocarbonate in 100 ml of water and then 74 g of ethyl chloroacetate were added thereto dropwise. The mixture was stirred for 2 hours and filtered. The filtrate was evaporated to dryness under reduced pressure and 2500 ml of water were added to the residue followed by addition of 70 ml of hydrogen peroxide (110 volumes). The mixture was stirred for 2 hours and the aqueous solution was washed with ethyl acetate and was acidified to a pH of 1 by addition of concentrated hydrochloric acid. The mixture was iced and vacuum filtered and the crystals recovered were washed and dried to obtain 48 g of 3-hydroxy-5-(ethoxycarbonylmethylthio)-1,2,4-thiadiazole melting at 131° C. A microanalytical sample melting at 131° C was obtained by crystallization from ethyl acetate.

Analysis: $C_6H_8N_2O_3S_2$: Calculated: %C 32.72, %H 3.66, %N 12.70, %S 29.12; Found: C 32.5, H 3.6, N 12.9, S 29.3.

STEP B: 2-(N-methylcarbamoyl)-5-(ethoxycarbonylmethylthio)-1,2,4-thiadiazole-3-one 10 ml of methyl isocyanate were added to a solution of 11 g of 3-hydroxy-5-(ethoxycarbonylmethylthio)-1,2,4-thiadiazole in 100 ml of tetrahydrofuran containing 0.5 ml of triethylamine and the mixture was stirred for 2 hours at 20° C. The mixture was evaporated to dryness under reduced pressure and the residue was empasted with ethyl acetate and vacuum filtered. The crystals were washed with water to obtain 10 g of 2-(N-methylcarbamoyl)-5-(ethoxycarbonylmethylthio)-1,2,4-thiadiazole-3-one which after crystallization from acetone melted at 163° C.

Analysis: $C_8H_{11}N_3O_4S_2$: Calculated: %C 34.65, %H 3.99, %N 15.15, %S 22.13; Found: C 34.6, H 4.0, N 15.1, S 22.9.

EXAMPLE 13

2-(N-methylcarbamoyl)-5-n-propoxy-1,2,4-thiadiazole-3-one

STEP A: sodium O-n-propyl-N-cyanothioimidocarbonate 280 g of potassium hydroxide in 2 liters of propanol were cooled to 20° C and 380 g of carbon disulfide were added thereto. The mixture was stirred for 2 hours and was vacuum filtered to obtain 624 g of potassium O-n-propyldithiocarbonate melting at 230° C. 429 g of the said product were dissolved in 1 liter of water and 369 g of dimethyl sulfate were added thereto at a temperature lower than 50° C. The mixture was stirred for 17 hours and the organic phase was decanted to obtain 338 g of methyl O-n-propyldithiocarbonate with a boiling point of 60° C at 1 mm Hg and a refractive index of $n_D^{20} = 1.5385$.

94.6 g of cyanamide were added to a solution of 51.7 g of sodium in 2 liters of propanol and the mixture was stirred for 15 minutes after which the 338 g of the above product were added thereto. The mixture was stirred for 24 hours at 35° C under a current of inert gas and was concentrated to dryness to obtain 416 g of sodium O-propyl-N-cyano-thioimidocarbonate.

STEP B: 3-hydroxy-5-n-propoxy-1,2,4-thiadiazole 450 ml of 30% hydrogen peroxide were added at 80° C over 2 hours to a solution of the product of Step A in 1 liter of water while keeping the mixture alkaline by addition of sodium hydroxide. The mixture was stirred for 24 hours, was cooled and was washed with ethyl acetate. The aqueous phase was acidified by addition by hydrochloric acid and was vacuum filtered. The recovered product was washed with water and dried to obtain 200 g of 3-hydroxy-5-n-propoxy-1,2,4-thiadiazole melting at 92° C.

STEP C: 2-(N-methylcarbamoyl)-5-n-propoxy-1,2,4-thiadiazole-3-one 10 ml of methyl isocyanate were added to a solution of 16.01 g of 3-hydroxy-5-n-propoxy-1,2,4-thiadiazole, 0.5 ml of triethylamine and 200 ml of tetrahydrofuran and the mixture was stirred for 20 hours at 20° C. The mixture was evaporated to dryness and the residue was twice crystallized from a 75-25 isopropyl ether-ethyl acetate mixture to obtain 12 g of 2-(N-methylcarbamoyl)-5-n-propoxy-1,2,4-thiadiazole-3-one melting at 112° C.

Analysis: $C_7H_{11}N_3O_3S$: Calculated: %C 38.70, %H 5.10, %N 19.34, %S 14.75; Found: C 38.9, H 5.4, N 19.4, S 14.7.

EXAMPLE 14

2-(N-methylcarbamoyl)-5-n-butoxy-1,2,4-thiadiazole-3-one 10 ml of methyl isocyanate were added to a solution of 17.5 g of 3-hydroxy-5-n-butoxy-1,2,4-thiadiazole in 125 ml of tetrahydrofuran containing 0.5 ml of triethylamine and after stirring for 2 hours at 20° C, the mixture was evaporated to dryness. The residue was empasted with isopropyl ether and was vacuum filtered and dried to obtain 21 g of 2-(N-methylcarbamoyl)-5-n-butoxy-1,2,4-thiadiazole-3-one melting at 108° C.

Analysis: $C_8H_{13}N_3O_3S$: Calculated: %C 41.55, %H 5.67, %N 18.17, %S 13.85; Found: C 41.2, H 5.7, N 18.1, S 14.0.

EXAMPLE 15

2-(N-methylcarbamoyl)-5-(p-chlorobenzyloxy)-1,2,4-thiadiazole-3-one

STEP A: potassium O-p-chlorobenzyl-N-cyanothioimidocarbonate 50 g of sodium hydride (in 50% suspension in mineral oil) were added to a mixture of 142 g of p-chlorobenzyl alcohol and 1200 ml of tetrahydrofuran and the mixture was refluxed for 2 hours and filtered. 76 g of carbon disulfide were added to the filtrate and the mixture was stirred for 30 minutes at 20° C and was evaporated to dryness. The residue was taken up in ether and was vacuum filtered to obtain 205 g of sodium O-p-chlorobenzyldithiocarbonate. A mixture of the latter product, 500 ml of benzene and 500 ml of methyl iodide was refluxed for 2½ hours and was then filtered. The filtrate was concentrated to dryness to obtain 196 g of methyl O-p-chlorobenzyldithiocarbonate.

34 g of cyanamide were added to a mixture of 60 g of potassium methylate and 700 ml of ethanol and after dissolution, 200 g of methyl O-p-chlorobenzyldithiocarbonate were added thereto. The mixture was stirred at 20° C for 17 hours and was vacuum filtered. The recovered crystals were washed with ether to obtain 126 g of potassium O-p-chlorobenzyl-N-cyanothioimidocarbonate melting at 240° C.

STEP B: 3-hydroxy-5-(p-chlorobenzyloxy)-1,2,4-thiadiazole

Potassium O-p-chlorobenzyl-N-cyanothioimidocarbonate was oxidized with hydrogen peroxide to obtain 3-hydroxy-5-(p-chlorobenzyloxy)-1,2,4-thiadiazole melting at 170° C.

STEP C: 2-(N-methylcarbamoyl)-5-(p-chlorobenzyloxy)-1,2,4-thiadiazole-3-one 5 ml of methyl isocyanate were added to a solution of 12.1 g of 3-hydroxy-5-(p-chlorobenzyloxy)-1,2,4-thiadiazole in 150 ml tetrahydrofuran and the mixture was stirred for 2 hours and 20° C and then concentrated to dryness. The residue was crystallized from ethyl acetate to obtain 7.3g of 2-(N-methylcarbamoyl)-5-(p-chlorobenzyloxy)-1,2,4-thiadiazole-3-one melting at 145° C.

Analysis: $C_{11}H_{10}ClN_3O_3S$: Calculated: %C 44.07, %H 3.36, %Cl 11.82, %N 14.01, %S 10.69; Found: C 44.1, H 3.4, Cl 11.9, N 14.1, S 10.6.

EXAMPLE 16

2-(N-methylcarbamoyl)-5-n-hexyloxy-1,2,4-thiadiazole-3-one

STEP A: potassium O-n-hexyl-N-cyano-thioimidocarbonate

A mixture of 325 g of potassium O-n-hexyloxydithiocarbonate [described by Warren et al., Anal. Chem., Vol. 26 (1954), p. 1985] in 500 ml of methyl iodide and 500 ml of benzene was refluxed for 18 hours and the mixture was filtered. The filtrate was evaporated to dryness and the residue was rectified under reduced pressure to obtain 278 g of O-n-hexyl-S-methyldithiocarbonate boiling at 100°-104° C at 0.5 mm Hg.

Analysis: $C_8H_{16}OS_2$: Calculated: %C 49.95, %H 8.38, %S 33.33; Found: C 49.9, H 8.3, S 32.90.

43 g of cyanamide were added to a solution of 70 g of potassium methylate in 100 methanol and 400 ml of ethanol cooled to 10° C and the mixture was stirred for 30 minutes. 192 g of O-n-hexyl-S-methyldithiocarbonate were added to the mixture and a current of nitrogen was passed therethrough to remove methyl mercaptan formed. The mixture was vacuum filtered and the recovered solid was washed with ethanol, the ether was dried to obtain 166 g of potassium O-n-hexyl-N-cyanothioimidocarbonate melting at 232° C.

STEP B: 3-hydroxy-5-(n-hexyloxy)-1,2,4-thiadiazole 130 ml of hydrogen peroxide were added dropwise over an hour at 70° C to a solution of 145.6 g of potassium O-n-hexyl-N-cyanothioimidocarbonate in 500 ml of water while keeping the pH between 8.3 and 8.7 by addition of concentrated potassium hydroxide and the mixture cooled to 0° C and filtered. The filtrate was washed with ether and acidified with hydrochloric acid. The mixture was vacuum filtered and the recovered precipitate was dissolved in ethyl acetate. The solution was dried and concentrated to dryness and the residue was dissolved in petroleum ether. The solution was cooled and vacuum filtered to obtain 72 g of 3-hydroxy-5-(n-hexyloxy)-1,2,4-thiadiazole melting at 61° C.

Analysis: $C_8H_{14}N_2O_2S$: Calculated: %C 47.50, %H 6.98, %N 13.85, %S 15.85; Found: C 47.6, H 7.2, N 14.00, S 15.7.

STEP C: 2-(N-methylcarbamoyl)-5-(n-hexyloxy)-1,2,4-thiadiazole-3-one 1 ml of triethylamine and 20 ml of methyl isocyanate were added to a solution of 15.3 g of 3-hydroxy-5-(n-hexyloxy)-1,2,4-thiadiazole in 150 ml of isopropyl ether and the mixture was stirred for 2 hours at 20° C and evaporated to dryness under reduced pressure. The residue was taken up in ether and the mixture was vacuum filtered. The precipitate was dried to obtain 19.1 g of 2-(N-methylcarbamoyl)-5-(n-hexyloxy-1,2,4-thiadiazole-3-one melting at 98° C.

Analysis: $C_{10}H_{17}N_3O_3S$: Calculated: %C 46.31, %H 6.60, %N 16.2, %S 12.36; Found C 46.5, H 6.7, N 16.3, S 12.1.

EXAMPLE 17

2-(N-methylcarbamoyl)-5-cyclohexyloxy-1,2,4-thiadiazole-3-one

STEP A: 3-hydroxy-5-cyclohexyloxy-1,2,4-thiadiazole 120 ml of ethanol were added to a solution of 17.82 g of sodium methylate in 35 ml of methanol and 13.87 g of cyanamide were added. The mixture stood for 30 minutes and then 62.8 g of O-cyclohexyl-S-methyldithiocarbonate [described by Taguchi et al, Tet., Vol. 18 (1962), p. 245] were added rapidly thereto. The mixture was stirred for 27 hours and was then concentrated to dryness. The residue was washed with isopropyl ether and dried to obtain 49 g of sodium O-cyclohexyl-N-cycanothioimidocarbonate melting at about 230° C.

47.5 ml of hydrogen peroxide (110 volumes) were slowly added at 70° C to a colution of 49 g of the said sodium salt in 140 ml of water while keeping the pH at 8.5 by addition of sodium hydroxide and after the temperature returned to 20° C, the mixture was filtered. The filtrate was acidified with hydrochloric acid and was extracted with ethyl acetate. The acetate extract was dried and evaporated to dryness and the residue was taken up in isopropyl ether. The mixture was iced and vacuum filtered and the recovered crystals were washed with pentane and dried to obtain 25 g of 3-hydroxy-5-cyclohexyloxy-1,2,4-thiadiazole melting at 105° C.

Analysis: $C_8H_{12}N_2O_2S$: Calculated: %C 47.98, %H 6.04, %N 13.98, %S 16.01; Found: C 47.9, H 6.1, N 13.9, S 16.0.

STEP B: 2-(N-methylcarbamoyl)-5-cyclohexyloxy-1,2,4-thiadiazole-3-one 1 ml of triethylamine and 6.7 g of methyl isocyanate were added to a solution of 14.01 g of 3-hydroxy-5-cyclohexyloxy-1,2,4-thiadiazole in 150 ml of tetrahydrofuran and the mixture was stirred for 2 hours at 20° C, treated with activated carbon, stirred and filtered. The filtrate was evaporated to dryness under reduced pressure and the residue was taken up in isopropyl ether. The mixture was vacuum filtered and the recovered crystals were dried to obtain 13.5 g of 2-(N-methylcarbamoyl)-5-cyclohexyloxy-1,2,4-thiadiazole-3-one melting at 121° C.

Analysis: $C_{10}H_{15}N_3O_3S$: Calculated: %C 46.67, %H 5.87, %N 16.33, %S 12.46; Found: C 46.8, H 6.0, N 16.3, S 12.4.

EXAMPLE 18

2-(N-methylcarbamoyl)-5-methylthio-1,2,4-thiadiazole-3-one

STEP A: 3-hydroxy-5-methylthio-1,2,4-thiadiazole

A mixture of 80 g of dipotassium N-cyanothioimido carbonate, 50.4 g of dimethyl sulfate and 500 ml of water was reacted at room temperature for 2 hours and was then filtered. 44 ml of 30% hydrogen peroxide was added dropwise to the filtrate and the mixture was acidified with 40 ml of concentrated hydrochloric acid. The mixture was cooled on an ice bath and was filtered. The recovered crystals were washed with water and dried to obtain 36 g of 3-hydroxy-5-methylthio-1,2,4-thiadiazole melting at 160° C.

STEP B: 2-(N-methylcarbamoyl)-5-methylthio-1,2,4-thiadiazole-3-one 0.1 ml of triethylamine and 5 ml of methyl isocyanate were added to a solution of 7.5 g of 3-hydroxy-5-methylthio-1,2,4-thiadiazole in 50 ml of tetrahydrofuran and after stirring at 20° C for 3 hours, 25 ml of isopropyl ether were added. The mixture was vacuum filtered and the recovered crystals were washed, dried and crystallized from acetone to obtain 5.2 g of 2-(N-methylcarbamoyl)-5-methylthio-1,2,4-thiadiazole-3-one melting at 144° C.

Analysis: $C_5H_7N_3O_2S_2$: Calculated: %C 29.26, %H 3.44, %N 20.47, %S 31.24; Found: C 29.3, H 3.4, N 20.4, S 31.5.

EXAMPLE 19

2-(N-methylcarbamoyl)-5-ethylthio-1,2,4-thiadiazole-3-one 10.4 ml of triethylamine and 10 ml of methyl isocyanate were added to a solution of 20.3 g of 3-hydroxy-5-ethylthio-1,2,4-thiadiazole in 100 ml of tetrahydrofuran and the mixture was stirred at 20° C for 1 hour, cooled to −10° C and filtered. The product was crystallized from ethyl acetate to obtain 18 g of 2-(N-methylcarbamoyl)-5-ethylthio-1,2,4-thiadiazole-3-one melting at 131° C.

Analysis: $C_6H_9N_3O_2S_2$: Calculated: %C 32.86, %H 4.13, %N 19.16, %S 29.25; Found: C 33.2, H 4.0, N 19.2, S 29.3.

EXAMPLE 20

2-(N-methylcarbamoyl)-5-allythio-1,2,4-thiadiazole-3-one

STEP A: 3-hydroxy-5-allylthio-1,2,4-thiadiazole 77 g of allyl chloride and 195 g of potassium N-cyanodithioimidocarbonate were condensed and the reaction product was oxidized with 100 ml of 30% hydrogen peroxide to obtain 63 g of 3-hydroxy-5-allylthio-1,2,4-thiadiazole melting at 84° C.

STEP B: 2-(N-methylcarbamoyl)-5-allylthio-1,2,4-thiadiazole-3-one 0.5 ml of triethylamine and 5 ml of methyl isocyanate were added to a solution of 13.9 g of 3-hydroxy-5-allylthio-1,2,4-thiadiazole in 150 ml of tetrahydrofuran and the mixture was stirred at 20° C for 2 hours and was concentrated to dryness under reduced pressure. The residue was empasted with ethyl ether and was vacuum filtered and dried to obtain 15.9 g of 2-(N-methylcarbamoyl)-5-allylthio-1,2,4-thiadiazole-3-one melting at 110° C.

Analysis: $C_7H_9N_3O_2S_2$: Calculated: %C 36.35, %H 3.93, %N 18.16, %S 27.73; Found: C 36.4, H 4.1, N 17.9, S 28.0.

EXAMPLE 21

2-(N-methylcarbamoyl)-5-(p-chlorobenzylthio)-1,2,4-thiadiazole-3-one

STEP A: 3-hydroxy-5-(p-chlorobenzylthio)-1,2,4-thiadiazole

A mixture of 144 g of potassium S-p-chlorobenzyl-N-cyano-dithioimidocarbonate, 48 ml of 30% hydrogen peroxide and 1000ml of water was heated to 65° C, returned to room temperature and filtered. The filtrate was acidified with 40 ml of concentrated hydrochloric acid and was filtered. The recovered crystals were washed with water and dried to obtain 90 g of 3-hydroxy-5-(p-chlorobenzylthio)-1,2,4-thiadiazole melting at 138° C.

STEP B: 2-(N-methylcarbamoyl)-5-(p-chlorobenzylthio)-1,2,4-thiadiazole-3-one 0.2 ml of triethylamine and 6 ml of methyl isocyanate were added to a solution of 12.9 g of 3-hydroxy-5-(p-chlorobenzylthio)-1,2,4-thiadiazole in 100 ml of tetrahydrofuran and after stirring the mixture for 2 hours at 20° C, isopropyl ether was added thereto. The mixture was filtered and the crystals were empasted with isopropyl ether and dried to obtain 15 g of 2-(N-methylcarbamoyl)-5-(p-chlorobenzylthio)-1,2,4-thiadiazole-3-one melting at 140° C.

Analysis: $C_{11}H_{10}ClN_3O_2S_2$: Calculated: %C 41.83, %H 3.21, %N 11.22, %Cl 13.31, %S 20.30; Found: C 41.8, H 3.1, N 11.5, Cl 13.7, 20.0.

EXAMPLE 22

2-(N-methylcarbamoyl)-5-dimethylamino-1,2,4-thiadiazole-3-one

STEP A: 3-hydroxy-5-dimethylamino-1,2,4-thiadiazole 180 ml of 10% dimethylamine in ether were added to a solution of 40 g of ethoxycarbonyl isothiocyanate in 200 ml of benzene and the mixture was stirred at 20°-25° C for 15 minutes. The solvent and excess dimethylamine were distilled to obtain an oil which crystallized which was N,N-diemthyl-N'-ethoxycarbonyl-thiourea with a melting point of 66° C and an Rf = 0.25 (silica benzene-ethyl acetate 9-1).

A solution of 43 g of N,N-dimethyl-N'-ethoxycarbonyl-thiourea, 25 ml of sodium hydroxide and 250 ml of water and a solution of 1M sodium hypochlorite were simultaneously added at 0° to 5° C to 450 ml of concentrated ammonium hydroxide and the reaction mixture was stirred for 2 hours at 0° to 5° C and 3 hours at room temperature. The mixture was evaporated until it congealed into a mass and the mass was adjusted to a pH of 4 with concentrated hydrochloric acid. The mixture was extracted with chloroform and the extracts were dried over magnesium sulfate and were evaporated to dryness. The crystalline residue was washed with petroleum ether (B.p. = 40°-75° C) to obtain 11 g of 3-hydroxy-5-dimethylamino-1,2,4-thiadiazole melting at 142° C and having a Rf = 0.2 (acetone -CHCl₃ - 1-1).

STEP B: 2-(N-methylcarbamoyl)-5-dimethylamino-1,2,4-thiadiazole-3-one 0.53 ml of triethylamine were added to a solution of 18 g of 3-hydroxy-5-dimethylamino-1,2,4-thiadiazole in 150 ml of chloroform and 11.5 g of methyl isocyanate were added thereto in small fractions. The mixture was stirred for 30 minutes at 20° C and was filtered and the filtrate was evaporated to dryness. The residue was crystallized from ethyl acetate to obtain 18.5 g of 2-(N-methylcarbamoyl)-5-dimethylamino-1,2,4-thiadiazole-3-one melting at 164° C.

Analysis: $C_6H_{10}N_4O_2S$: Calculated: %C 35.63, %H 4.98, %N 27.70, %S 15.85; Found: C 35.6, H 5.0, N 27.9, S 15.8.

EXAMPLE 23

2-(N-methylcarbamoyl)-5-phenyl-1,2,4-thiadiazole-3-one 0.5 ml of triethylamine and 10 ml of methyl isocyanate were added to a solution of 9 g of 3-hydroxy-5-phenyl-1,2,4-thiadiazole in 100 ml of tetrahydrofuran and the mixture was stirred at 20° C for an hour and then was vacuum filtered. The crystals recovered were crystallized from acetic acid to obtain 10 g of 2-(N-methylcarbamoyl)-5-phenyl-1,2,4-thiadiazole-3-one melting at 210° C.

Analysis: $C_{10}H_9N_3O_2S$: Calculated: %C 51.05, %H 3.85, %N 17.86, %S 13.63; Found: 51.1, H 3.9, N 17.8, S 13.7.

EXAMPLE 24

2-(N-methylcarbamoyl)-5-n-butylthio-1,2,4-thiadiazole-3-one

STEP A: 3-hydroxy-5-n-butylthio-1,2,4-thiadiazole 42 ml of hydrogen peroxide (110 volumes) were added over 1½ hours at 50° C to a solution of 90 g of potassium n-butyl-N-cyanodithiocarbonate [described in U.S. Pat. No. 3,658,901] in 300 ml of water and the mixture was filtered. The filtrate was acidified with an aqueous hydrochloric acid solution and the mixture was vacuum filtered. The recovered precipitate was washed with water, dried and crystallized from isopropyl ether to obtain 26 g of 3-hydroxy-5-n-butylthio-1,2,4-thiadiazole melting at 78° C.

Analysis: $C_6H_{10}N_2O_2S_2$: Calculated %C 37.87 %H 5.29 %N 14.72, %S 33.7; Found: C 37.7, H 5.4, N 14.6, S 33.7.

STEP B: 2-(N-methylcarbamoyl)-5-n-butylthio-1,2,4-thiadiazole-3-one 0.5 ml of triethylamine and 4.78 g of methyl isocyanate were added to a solution of 95 g of 3-hydroxy-5-n-butylthio-1,2,4-thiadiazole in 50 ml of isopropyl ether and the mixture was stirred for 2 hours at 20° C and was vacuum filtered. The recovered precipitate was washed with isopropyl ether and dried to obtain 11.2 g of 2-(N-methylcarbamoyl)-5-n-butylthio-1,2,4-thiadiazole-3-one melting at 102° C.

Analysis: $C_8H_{13}N_3O_2S_2$: Calculated: %C 38.84, %H 5.29, %N 16.98, %S 25.92; Found: C 39.0, H 5.5, N 17.0, S 26.0.

EXAMPLE 25

2-(N-vinylcarbamoyl)-5-ethoxy-1,2,4-thiadiazole-3-one 1 ml of triethylamine was added to a solution of 14.6 g of 3-hydroxy-5-ethoxy-1,2,4-thiadiazole in 250 ml of isopropyl ether and after 5 minutes, 8 g of vinyl isocyanate were added. The mixture was stirred for 30 minutes at 20° C and was vacuum filtered and the recovered precipitate was washed, dried and crystallized from ethyl acetate to obtain 15 g of 2-(N-vinylcarbamoyl)-5-ethoxy-1,2,4-thiadiazole-3-one melting at 123° C.

Analysis: $C_7H_9N_3O_3S$: Calculated: %C 39.06, %H 4.22, %N 19.52, %S 14.90; Found: C 39.0, H 4.2, N 19.7, S 14.6.

EXAMPLE 26

2-(N-methylcarbamoyl)-5-isopropyloxy-1,2,4-thiadiazole-3-one

STEP A: 3-hydroxy-5-isopropoxy-1,2,4-thiadiazole 250 ml of ethanol and 33.2 g of cyanamide were added to a solution of 55.4 g of potassium methylate in 230 ml of methanol and then 118.7 g of O-isopropyl-S-methyl-dithiocarbonate were added. The mixture was stirred for 15 hours at 20° C while removing the freed methyl mercaptan. The mixture was evaporated to dryness and isopropyl ether was added to the residue. The mixture was stirred and vacuum filtered to obtain 119 g of potassium O-isopropyl-N-cyano-thioimidocarbonate melting at 192° C.

60 ml of hydrogen peroxide (110 volumes) and 120ml of an aqueous 1N potassium hydroxide solution were simultaneously added over 45 minutes at 63° C and a pH of 8.5 to a solution of 54.7 g of potassium O-isopropyl-N-cyano-thioimidocarbonate in 200 ml of water. The reaction mixture was washed with ethanol and acidified with 35 ml of concentrated hydrochloric acid. The mixture was extracted with ethyl acetate and the extracts were evaporated to dryness. The residue was taken up in isopropyl ether and the mixture was vacuum filtered to obtain 20 g of 3-hydroxy-5-isopropoxy-1,2,4-thiadiazole melting at 74° C.

Analysis: $C_5H_8N_2O_2S$: Calculated: %C 37.50, %H 5.03 %N 17.49, %S 19.97; Found: C 37.5, H 5.2, N 17.5, S 19.6.

STEP B: 2-(N-methylcarbamoyl)-5-isopropoxy-1,2,4-thiadiazole-3-one

A mixture of 17.6 g of 3-hydroxy-5-isopropoxy-1,2,4-thiadizole, 140 ml of isopropyl ether, 1 ml of triethylamine and 11 ml of methyl isocyanate was stirred for 20 hours at 20° C and was vacuum filtered. The recovered crystals were washed with isopropyl ether to obtain 20 g of 2-(N-methylcarbamoyl)-5-isopropoxy-1,2,4-thiadiazole-3-one melting at 95° C.

Analysis: $C_7H_{11}N_3O_3S$: Calculated %C 38.71, H 5.1, %N 19.34, %S 14.76; Found: C 38.7, H 5.1, N 19.3, S 14.9.

EXAMPLE 27

An emulsifiable herbicidal concentrate was prepared from 400 g of 2-(N-methylcarbamoyl)-5-ethoxy-1,2,4-thiadiazole-3-one, 84 g of Atlox 4851 (alkykl aryl sulfonate mixed with polyoxythylene triglyceride-viscosity of 300–700 cps at 25° C), 56 g of Atlox of 4855 (alkyl aryl sulfonate mixed with polyoxyethylene triglyceride-viscosity of 1500–1900 cps at 25° C), 300 g of xylene and 160 g of cyclohexanone.

HERBICIDAL ACTIVITY

The post emergence herbicidal activity was determined with 2-(N-methylcarbamoyl)-5-allythio-1,2,4-thiadiazole-3-one (compound A), 2-(N-methylcarbamoyl)-5-n-butoxy-1,2,4-thiadiazole-3-one (compound B), 2-(N-methylcarbamoyl)-5-ethoxy-1,2,4-thidiazole-3-one (compound C) and 2-(N-methylcarbamoyl)-5-ethylthio -1,2,4-thiadiazole-3-one (compound D).

The test species were cultivated in a culture flat (23 × 14 × 4 cm) with a double bottom and means for watering from below. The species were placed in a single flat at a ratio of 20 seeds per species in rows spaced 3cm apart and 4 flats were used for each compound and each concentration. The growing conditions were: temperature of 20° C ± 2° C, about 60% humidity, lighting by a fluorescent tube (day light + brilliant white) from 6 to 22 hours per day. The soil mixture was 10 volumes of earth, 10 volumes of river sand and 2 volumes of peat.

The post-emergence tests were effected 21 days after the seed planting on the aerial parts with the test products applied under standard conditions with a microsprayer at doses of 5, 2.5, 1.25 and 0.625 kg/ha and at a dilution of 560 l/ha. The final results were determined from the number of plants 21 days after treatment and the results were expressed as a percentage of reduction in the number of plants (percentage of mortality) calculated as follows:

$$M = \frac{\text{No. of control plants} - \text{No. of treated plants}}{\text{No. of control plants}} \times 100$$

COMPOUND A

| Plant Species | Doses in Kg/ha | | | |
|---|---|---|---|---|
| | 5 | 2.5 | 1.25 | 0.625 |
| Triticum Sativum | 0 | 0 | 0 | 0 |
| Hordeum Spec | 0 | 0 | 0 | 0 |
| Zea Mays | 0 | 0 | 0 | 0 |
| Avena Fatua | 0 | 0 | 0 | 0 |
| Agrostis Tenuis | 0 | 0 | 0 | 0 |
| Lolium Perenne | 100 | 72 | 27 | 0 |
| Alopecurus Myosuroides | 0 | 0 | 0 | 0 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 100 | 100 | 100 | 100 |
| Sinapis Alba | 100 | 100 | 100 | 100 |
| Rumex Crispus | 100 | 100 | 100 | 100 |
| Trifolium Praetense | 100 | 100 | 100 | 100 |

COMPOUND B

| Plant Species | Doses in Kg/ha | | | |
|---|---|---|---|---|
| | 5 | 2.5 | 1.25 | 0.625 |
| Triticum Sativum | 23 | 0 | 0 | 0 |
| Hordeum Spec | 100 | 100 | 50 | 0 |
| Zea Mays | 0 | 0 | 0 | 0 |
| Avena Fatua | 100 | 100 | 100 | 28 |
| Agrostis Tenuis | 100 | 100 | 100 | 100 |
| Lolium Perenne | 100 | 100 | 100 | 100 |
| Alopecurus Myosuroides | 100 | 100 | 100 | 30 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 90 | 86 | 31 | 0 |
| Sinapis Alba | 100 | 100 | 100 | 100 |
| Rumex Crispus | 100 | 100 | 100 | 48 |
| Trifolium Praetense | 100 | 100 | 100 | 83 |

COMPOUND C

| Plant Species | Doses in Kg/ha | | | |
|---|---|---|---|---|
| | 5 | 2.5 | 1.25 | 0.625 |
| Triticum Sativum | 0 | 0 | 0 | 0 |
| Hordeum Vulgare | 59 | 0 | 0 | 0 |
| Zea Mays | 0 | 0 | 0 | 0 |
| Avena Sativa | 70 | 0 | 0 | 0 |
| Agrostis Tenuis | 94 | 89 | 70 | 67 |
| Lolium Perenne | 100 | 73 | 0 | 0 |
| Alopecurus Myosuroides | 88 | 66 | 28 | 0 |
| Beta Vulgaris | 100 | 100 | 100 | 97 |
| Chenopodium Quinoa | 100 | 100 | 100 | 100 |
| Chrysanthemum Coronarium | 100 | 100 | 100 | 100 |
| Galium Aparine | 41 | 0 | 0 | 0 |
| Sinapis Alba | 100 | 100 | 100 | 94 |
| Rumex Crispus | 100 | 87 | 37 | 0 |
| Trifolium Praetense | 100 | 73 | 46 | 57 |

COMPOUND D

| Plant Species | Doses in Kg/ha | | | |
|---|---|---|---|---|
| | 5 | 2.5 | 1.25 | 0.625 |
| Triticum Sativum | 0 | 0 | 0 | 0 |
| Hordeum Vulgare | 0 | 0 | 0 | 0 |
| Zea Mays | 0 | 0 | 0 | 0 |
| Avena Sativa | 0 | 0 | 0 | 0 |
| Agrostis Tenuis | 35 | 50 | 48 | 0 |
| Lolium Perenne | 83 | 75 | 49 | 0 |
| Alopecurus Myosuroides | 0 | 0 | 0 | 0 |
| Beta Vulgaris | 100 | 100 | 100 | 84 |
| Chenopodium Quinoa | 96 | 100 | 97 | 65 |
| Chrysanthemum Coronarium | 100 | 100 | 98 | 87 |
| Galium Aparine | 46 | 33 | 35 | 0 |
| Sinapis Alba | 100 | 100 | 100 | 74 |
| Rumex Crispus | 100 | 100 | 66 | 23 |
| Trifolium Praetense | 96 | 82 | 20 | 0 |

The results of the Tables show that the compounds have an interesting post-emergence herbicidal activity and generally the products show a selective activity for graminous plants which are not attacked or only slightly at the doses at which the dicotyledons representing the weeds are destroyed.

Various modifications of the products and methods of the invention may be made without departing from the

We claim:

1. A compound of the formula

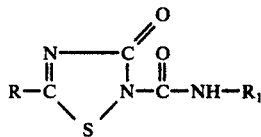

wherein R is selected from the group consisting of alkoxy of 1 to 8 carbon atoms, cycloalkyloxy of 3 to 7 carbon atoms, alkylthio of 1 to 8 carbon atoms optionally substituted with carbalkoxy of 2 to 5 carbon atoms, alkenylthio of 2 to 4 carbon atoms, and benzyloxy, benzylthio, benzyl and phenyl all aryl being optionally substituted with 1 to 2 members of the group consisting of chlorine, bromine, alkyl of 1 to 3 carbon atoms and alkoxy of 1 to 3 carbon atoms and $R_1$ is selected from the group consisting of alkyl of 1 to 6 carbon atoms optionally substituted with a member of the group consisting of chlorine, bromine and alkyloxy of 1 to 4 carbon atoms, alkenyl of 2 to 4 carbon atoms optionally substituted with 1 to 3 chlorine atoms or alkoxy of 1 to 3 carbon atoms.

2. A compound of claim 1 wherein $R_1$ is alkyl of 1 to 6 carbon atoms optionally substituted with a member of the group consisting of bromine, chlorine and alkoxy of 1 to 4 carbon atoms.

3. A compound of claim 1 wherein $R_1$ is alkyl of 1 to 6 carbon atoms and R is alkoxy of 1 to 8 carbon atoms.

4. A compound of claim 1 wherein $R_1$ is alkyl of 1 to 6 carbon atoms and R is alkylthio of 1 to 8 carbon atoms.

5. A compound of claim 1 wherein $R_1$ is alkyl of 1 to 6 carbon atoms and R is alkenylthio of 2 to 4 carbon atoms.

6. A compound of claim 1 which is 2-(N-methylcarbamoyl)-5-allylthio-1,2,4-thiadiazole-3-one.

7. A compound of claim 1 which is 2-(N-methylcarbamoyl)-5-n-butoxy-1,2,4-thiadiazole-3-one.

8. A compound of claim 1 which is 2-(N-methylcarbamoyl)-5-ethoxy-1,2,4-thiadiazole-3-one.

9. A compound of claim 1 which is 2-(N-methylcarbamoyl)-5-ethylthio-1,2,4-thiadiazole-3-one.

10. A compound of claim 1 which is 2-(N-methylcarbamoyl)-5-n-propoxy-1,2,4-thiadiazole-3-one.

11. A compound of claim 1 which is 2-(N-methylcarbamoyl)-5-n-hexyloxy-1,2,4-thiadiazole-3-one.

12. A compound of claim 1 which is 2-(N-methylcarbamoyl)-5-n-butylthio-1,2,4-thiadiazole-3-one.

13. A compound of claim 1 which is 2-(N-methylcarbamoyl)-5-isopropoxy-1,2,4-thiadiazole-3-one.

14. An herbicidal composition comprising an herbicially effective amount of a compound of formula I and an inert carrier.

15. A composition of claim 14 wherein $R_1$ is alkyl of 1 to 6 carbon atoms and R is selected from the group consisting of alkoxy of 1 to 8 carbon atoms, alkylthio of 1 to 8 carbon atoms and alkenylthio of 2 to 4 carbon atoms.

16. A method of killing plants comprising applying to plants an herbicidally effective amount of a compound of claim 1.

17. The method of claim 16 wherein $R_1$ is alkyl of 1 to 6 carbon atoms and R is selected from the group consisting of alkoxy of 1 to 8 carbon atoms, alkylthio of 1 to 8 carbon atoms and alkenylthio of 2 to 4 carbon atoms.

18. The method of claim 16 wherein the compound is 2-(N-methylcarbamoyl)-5-isopropoxy-1,2,4-thiadiazole-3-one.